(12) United States Patent
Martin et al.

(10) Patent No.: US 8,846,406 B1
(45) Date of Patent: Sep. 30, 2014

(54) DYNAMIC TUNING OF CHEMIRESISTOR SENSITIVITY USING MECHANICAL STRAIN

(75) Inventors: James E. Martin, Tijeras, NM (US); Douglas H. Read, Bosque Farms, NM (US)

(73) Assignee: Sandia Corporation, Albuquerque, NM (US)

(*) Notice: Subject to any disclaimer, the term of this patent is extended or adjusted under 35 U.S.C. 154(b) by 113 days.

(21) Appl. No.: 13/353,941

(22) Filed: Jan. 19, 2012

Related U.S. Application Data

(60) Provisional application No. 61/440,726, filed on Feb. 8, 2011.

(51) Int. Cl.
*G01N 27/00* (2006.01)
(52) U.S. Cl.
USPC ............... 436/149; 422/82.01; 422/82.02
(58) Field of Classification Search
USPC ........ 436/149; 205/775; 204/400; 422/82.01, 422/82.02
See application file for complete search history.

(56) References Cited

U.S. PATENT DOCUMENTS

2010/0276302 A1* 11/2010 Raguse et al. ............... 205/775

OTHER PUBLICATIONS

Controlling percolation in field-structured particle composites: Observations of giant thermoresistance, piezoresistance, and chemiresistance. James E. Martin, Robert A. Anderson, Judy Odinek, Douglas Adolf, and Jennifer Williamson Physical Review B 67, 094207, 2003.*

* cited by examiner

*Primary Examiner* — Vickie Kim
*Assistant Examiner* — Dwan A Gerido
(74) *Attorney, Agent, or Firm* — Kevin W. Bieg

(57) ABSTRACT

The sensitivity of a chemiresistor sensor can be dynamically tuned using mechanical strain. The increase in sensitivity is a smooth, continuous function of the applied strain, and the effect can be reversible. Sensitivity tuning enables the response curve of the sensor to be dynamically optimized for sensing analytes, such as volatile organic compounds, over a wide concentration range.

12 Claims, 7 Drawing Sheets

DYNAMIC TUNING OF CHEMIRESISTOR SENSITIVITY USING MECHANICAL STRAIN

CROSS-REFERENCE TO RELATED APPLICATION

This application claims the benefit of U.S. Provisional Application No. 61/440,726, filed Feb. 8, 2011, which is incorporated herein by reference.

STATEMENT OF GOVERNMENT INTEREST

The United States Government has rights in this invention pursuant to Department of Energy Contract No. DE-AC04-94AL85000 with Sandia Corporation.

BACKGROUND OF THE INVENTION

A chemiresistor is a particle composite whose electrical conductivity changes in the presence of particular chemical vapors known as analytes (typically volatile organic compounds). The magnitude of this observed resistance change is related to the concentration of analyte vapor in the environment. In general, the chemiresistor composite can comprise a plurality of conductive particles in a continuous electrically insulating matrix. Chemiresistor composites traditionally comprise carbon-black particles, which are randomly distributed in an amorphous (non-crosslinked) polymer matrix.

One type of chemiresistor device is known as a field-structured chemiresistor (FSCR). FSCRs contain particles that have a magnetic core and a conductive shell and are fabricated by mixing a particular volume fraction of these particles with a viscous elastomer precursor. This particle suspension is then subjected to a magnetic field and the particles form a structured network due to their dipole-dipole interactions. The elastomer is then cured and the magnetic field is removed, resulting in a permanently structured, electrically conductive composite. Field structuring brings the particles to the electrical conduction (percolation) threshold largely independent of particle volume fraction, whereas traditional chemiresistors require a high volume fraction of particles to conduct. Field-structuring of the particle phase can improve the response and reproducibility of the sensors. It is noteworthy that FSCRs can employ a cross-linked elastomer as the continuous matrix of the composite. FSCRs employing cross-linked elastomers have the useful property of reversible strain. With an elastomeric matrix, a particular analyte concentration does not necessarily irreversibly swell the matrix, and the matrix can shrink when the analyte concentration is reduced. This is often not the case with other types of chemiresistors and is one of the contributing factors to FSCR reversibility. FSCRs can exhibit high sensitivity, excellent sensor-to-sensor reproducibility, negligible irreversibility, and increased baseline stability.

When a chemiresistor is exposed to chemical vapors, the composite swells due to the absorption of these vapors into the polymer matrix. This swelling-induced isotropic strain causes the particle network to pull apart, breaking electrically conducting pathways and diminishing inter-particle contact pressure, thereby increasing contact resistance. This leads to a measurable increase in the composite's overall resistance. The observed resistance change is correlated to the concentration of analyte in the environment through the transduction or response curve. The response of an FSCR can be described as a function of analyte concentration in terms of its relative conductance ratio, $G/G_o$, where $G_o$ is the conductance of an FSCR in the absence of analyte and G is the conductance at a particular analyte concentration (at thermodynamic equilibrium). Plotting $G/G_o$ as a function of analyte concentration results in a sigmoidal curve as seen in FIG. 1(a). FSCR sensitivity is the slope of the transduction curve at a specific analyte concentration. It is seen from FIG. 1(b) that the sensitivity of an FSCR varies over the range of analyte concentrations; the maximum sensitivity occurs around the inflection point of the curve (mid-point response or $G/G_o=0.5$), whereas at the upper and lower limits of the sensing range the sensitivity is extremely low.

With conventional chemiresistors, obtaining sufficient sensitivity over an extended range of concentration requires having several different chemiresistors, each comprising a film permanently tuned to a different portion of the extended range. A single conventional chemiresistor is not able to provide sensitivity over a wide range of analyte concentrations because range tunability was not a characteristic of conventional chemiresistors.

Therefore, a need remains for a single chemiresistor that can provide sensitivity over a wide range of analyte concentrations.

SUMMARY OF THE INVENTION

The present invention is directed to a sensor and method for dynamic tuning of chemiresistor sensitivity using mechanical strain. The chemiresistor sensor comprises a chemiresistor composite, and an apparatus for applying mechanical strain to chemiresistor composite and measuring the conductance of the strained chemiresistor composite. The chemiresistor composite can comprise a plurality of conducting particles in a strainable electrically insulating matrix. The conducting particles can comprise gold, silver, platinum, copper, carbon, ferrite, cobalt, nickel, iron, gadolinium, chromium, or manganese. The chemiresistor composite can comprise a field-structured composite, wherein the field-structured composite comprises conducting magnetic particles in a polymeric matrix. The conducting magnetic particles can comprise a conductive outer shell surrounding a magnetic core, wherein the magnetic core comprises ferrite, cobalt, nickel, iron, gadolinium, chromium, or manganese. The mechanical strain can be a uniaxial strain, shear strain, torsional strain, or combination thereof. The sensor can further comprise a flexible substrate, such as a polymer, attached to the chemiresistor composite. The sensor can further comprise a pair of electrodes having a gap therebetween, and wherein the conductance of the chemiresistor composite is measured across the gap between the pair of electrodes. The sensor can further comprise a means for exposing the chemiresistor composite to an analyte, such as a flowcell.

The invention is further directed to a method for determining the concentration of an analyte with a chemiresistor sensor, comprising a chemiresistor composite; applying a mechanical strain to chemiresistor composite; exposing the strained chemiresistor composite to the analyte; and measuring the conductance of the exposed chemiresistor composite to determine the concentration of the analyte. A baseline conductance of the strained chemiresistor composite can be measured prior to the exposing step and the measured conductance of the analyte-exposed chemiresistor composite can be compared to the baseline conductance. The chemiresistor composite can be strained (prior to analyte exposure) to optimize the sensitivity of the sensor to the analyte.

As an example of the present invention, a FSCR sensor can be used to detect volatile organic compounds and whose sensitivity can be reversibly increased over a range of nearly two decades by the application of a tensile strain. This polymer-based sensor is comprised of Au-plated magnetic particles structured into conducting chains by the application of a magnetic field during the curing of the prepolymer resin. The resistance of this field-structured composite increases when an analyte vapor swells the polymer and reduces the contact pressure between particles. Applying a tensile strain increases both the sensor resistance and sensitivity to subsequent analyte exposure, as defined by its relative change in conductance. This increase in sensitivity is a smooth, continuous function of the applied strain, and the effect is reversible when the strain is decreased. Sensitivity tuning enables the response curve of the sensor to be dynamically optimized for sensing analytes over a wide concentration range.

BRIEF DESCRIPTION OF THE DRAWINGS

The accompanying drawings, which are incorporated in and form part of the specification, illustrate some embodiments of the present invention and, together with the description, serve to explain the principles of the invention.

DETAILED DESCRIPTION OF THE INVENTION

Figure 1:
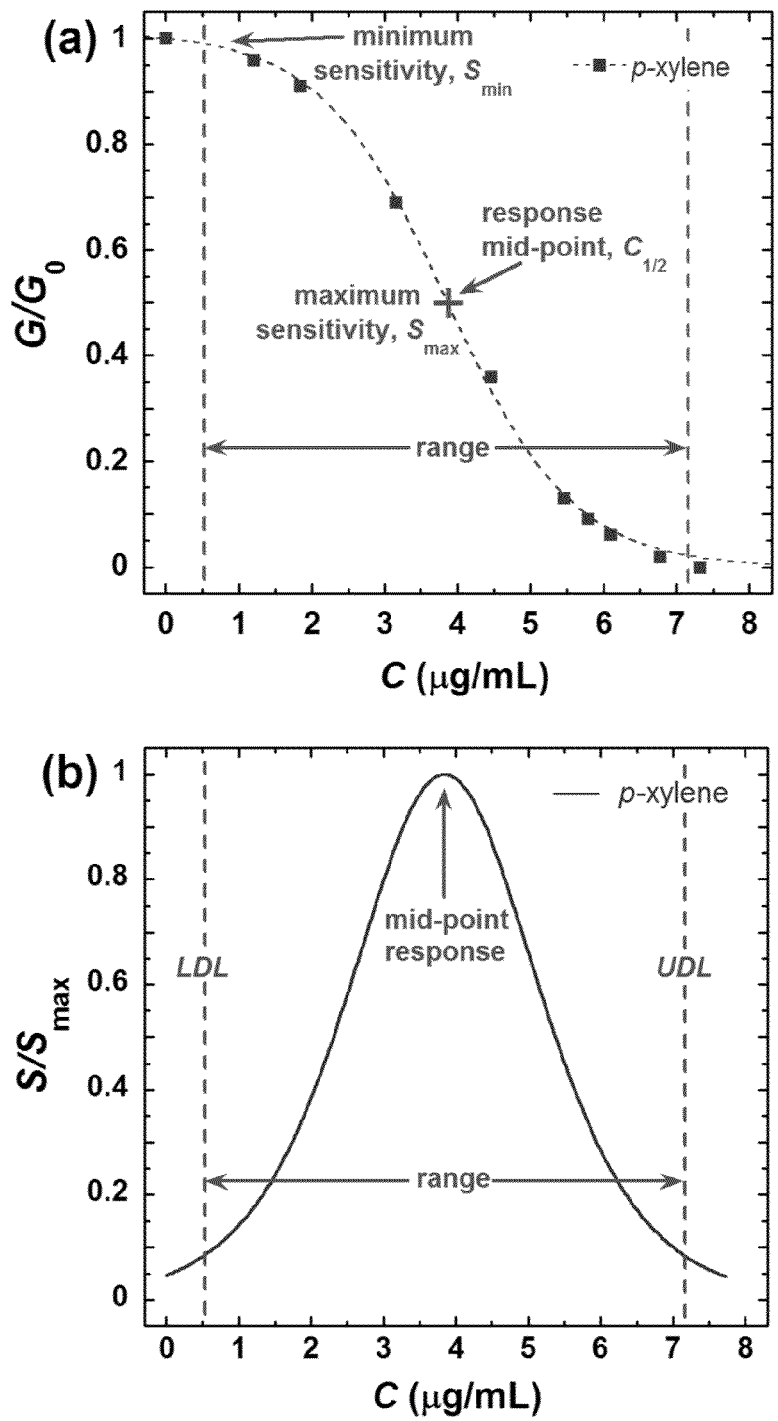
FIG. 1(a) is a graph of relative conductance ratio versus analyte concentration for the field-structured chemiresistor.
FIG. 1(b) is a graph of sensitivity versus analyte concentration for the field-structured chemiresistor.

This invention is directed to a resistance-based chemical sensor (chemiresistor) device with tunable sensitivity that enables selection of different sensitivity ranges of operation for a single chemiresistor device. The sensitivity can be reversibly varied over a range of approximately two decades by the application of strain.

The electrical conductivity of a chemiresistor is sensitive to strain of various types, including uniaxial strain (tensile and/or compressive), shear, and volumetric. In some embodiments of this invention, the resistive composite is mechanically strained to a lower initial conductance in the absence of an analyte. This produces a shift of the sensor's conductance baseline to one that is farther along the transduction curve where there is a higher sensitivity to the analyte. Varying the magnitude of mechanically induced strain enables reversible alteration of the sensor to selectively tune the sensor's sensitivity to a desired range. Embodiments employing field-structured composites (FSCs) as the sensing material are described herein, but it is to be understood that the invention described herein is also applicable to many other types of chemiresistors using sensing films that are not field-structured composites, and embodiments comprising such alternative sensing films are intended to be included within the scope of this invention.

In some embodiments, the polymer-based sensor comprises gold-plated magnetic particles structured into conducting chains by the application of a magnetic field during cure of the prepolymer resin. The resistance of this field-structured composite increases when an analyte vapor swells the polymer and reduces the contact pressure between particles. Applying a tensile strain has been shown to increase both the sensor resistance and sensor sensitivity to subsequent analyte exposure. Sensitivity is defined as the magnitude of the sensor's relative resistance change in response to a particular change in analyte concentration. This increase in sensitivity is a smooth, continuous function of the applied strain, and the effect is fully reversible. Sensitivity tuning enables the response curve of the sensor to be dynamically optimized for sensing analytes over a wide concentration range.

In some embodiments, FSCs are formed wherein the conducting phase (including but not restricted to Au-coated or Ag-coated particles of Ni, Fe, Co, or Gd and/or to other conducting magnetic particles) is structured into chains by the application of a magnetic field during polymer cure. These chains form over a broad range of particle loadings, and this structuring process yields chemiresistors with highly reproducible conductivities and sensitivities, negligible irreversibility, and insignificant baseline drift. However, the sigmoidal response curve (conductance versus analyte concentration) of a typical, unstrained chemiresistor is relatively flat at low analyte concentrations, so the sensor is insensitive at low analyte concentrations. An illustrative response curve is presented in FIG. 1(a). The following US Patents and Patent Application regarding FSCRs are incorporated herein by reference: Martin et al., U.S. Pat. No. 6,194,769; Martin et al., U.S. Pat. No. 6,290,868; Martin et al., U.S. Pat. No. 6,391,393; Martin et al., U.S. Pat. No. 6,844,378; and Martin and Read, U.S. patent application Ser. No. 11/681,221.

In embodiments of this invention, a means for controllably and variably applying a tensile strain to the sensor is employed to greatly increase its sensitivity in the low-concentration regime. This effect is fully reversible and enables the development of an actuator-controlled chemiresistor that can accurately sense over a range of more than three orders of magnitude of analyte concentration. Embodiments employing FSC sensing films are discussed herein, but it is to be understood that embodiments employing sensing films that are not field-structured composites are also included within the scope of this invention.

In various embodiments, chemiresistor sensitivity is increased by mechanically straining the sensor film to obtain a lower initial conductance in the absence of an analyte. This can produce a shift of the sensor's conductance baseline to one that is farther along the transduction curve where the sensor has a higher sensitivity to the analyte. Adjustment of the amount of mechanical strain enables reversible alteration of the sensor sensitivity to tune the sensor to a desired target sensitivity using the same sensor film.

Figure 2:
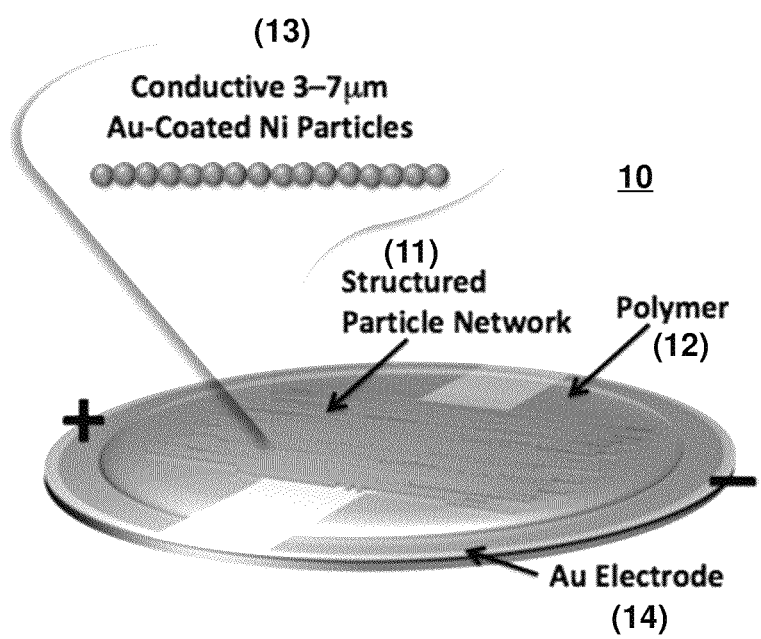
FIG. 2 is a schematic illustration of a field-structured chemiresistor sensor.

A schematic illustration of an exemplary sensor is shown in FIG. 2. In this example, the chemiresistor sensor 10 comprises a chemiresistor composite 11 that can be mechanically strained to a desired baseline (pre-analyte) conductance. The chemiresistor composite 11 comprises a plurality of conducting particles in a continuous strainable electrically insulating matrix. For example, the conducting particles can comprise gold, silver, platinum, copper, carbon, ferrite, cobalt, nickel, iron, gadolinium, chromium, or manganese. The chemiresistor can be a FSCR, in which case the chemiresistor composite can comprise conducting magnetic particles in a polymeric matrix. The conducting magnetic particles can comprise a conductive outer shell surrounding a magnetic core. For example, the magnetic core can comprise ferrite, cobalt, nickel, iron, gadolinium, chromium, or manganese. The sensor 10 can incorporate a flexible substrate 12 to which the chemiresistor composite 11 is bonded. The flexible substrate 12 in some embodiments can be a polymer, such as polydimethylsiloxane (PDMS), but other flexible substrates can also be employed. The bonding of the composite 11 to the flexible substrate 12 can be chemical or physical. The conductance of the chemiresistor composite 11 can be measured between a pair of electrodes 14. With a FSCR, the particles 13 can be oriented, for example to span the electrode gap. The electrodes 14 can be of a variety of compositions; in some embodiments, a gold mesh can be employed. The electrodes 14 can be partially encapsulated between the sensor film and the flexible substrate.

In some embodiments employing a field structured composite sensor film, the chemiresistor composite and gold-mesh electrodes can be bonded to the substrate by placing them on the elastomeric substrate just before the substrate is fully cured (i.e. just after it has reached its gel point). At this point, the substrate is still tacky to the touch but is sufficiently solidified to be able to support the electrodes and the uncured, viscous, chemiresistor composite precursor. Because the substrate is not fully cured, a fraction of unreacted functional groups are able to chemically bond with the curing chemiresistor composite. Chemical bonding of the chemiresistor to the substrate allows any straining of the substrate to be transferred directly to the chemiresistor with no slippage or delamination. This method has the added benefit of partially encapsulating the gold-mesh electrodes between the substrate and chemiresistor composite, which provides mechanical robustness. Using an elastomer as the substrate and as the continuous phase of the chemiresistor composite also enables the induced strain to be reversible. This is because elastomers can typically be stretched between five to ten times their original lengths with essentially complete reversibility. Although an elastomer is used in some embodiments, the scope of this invention includes the use of any substrate materials that can be strained.

Figure 3:
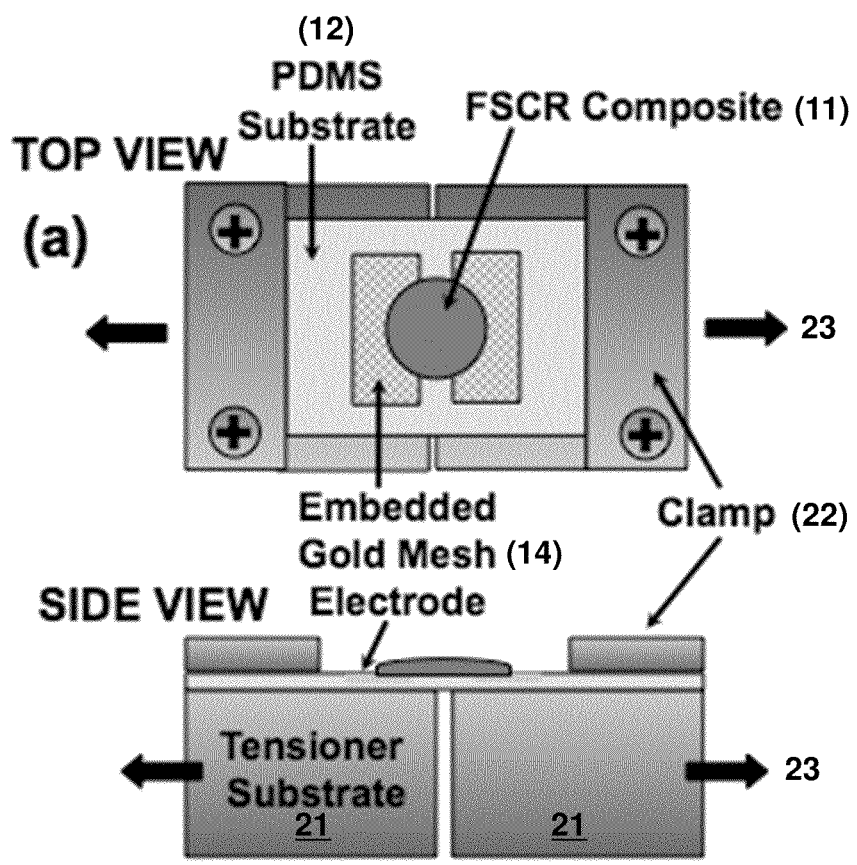
FIG. 3 is a schematic illustration of a mechanical strain apparatus comprising a split-substrate tensioner and also detailing the strainable chemiresistor and elastomeric substrate.

As shown in FIG. 3, in some embodiments, a mechanical strain apparatus 20 for applying mechanically strain the chemiresistor composite 11 can comprise two adjacent and possibly abutting but separable structures 21 with surfaces on which the elastomeric substrate 12 is clamped 22 at each end. The separable surfaces can be held together by a compressed spring until they are pushed apart by a strain-applying means 23. A device such as a micrometer-calibrated screw can be employed to push the surfaces apart, stretching the affixed elastomeric substrate 12 and bonded chemiresistor sensing film 11 between electrodes 14. Alternative strain-applying structures can be used in different embodiments. Embodiments of this invention can employ any of a wide range of devices to mechanically strain the chemiresistor. These include but are not limited to piezoelectric actuators, magnetostrictive materials, electrical motors, pneumatic actuators, hydraulic pistons, solenoids, comb drives, and electroactive polymers.

Figure 4:
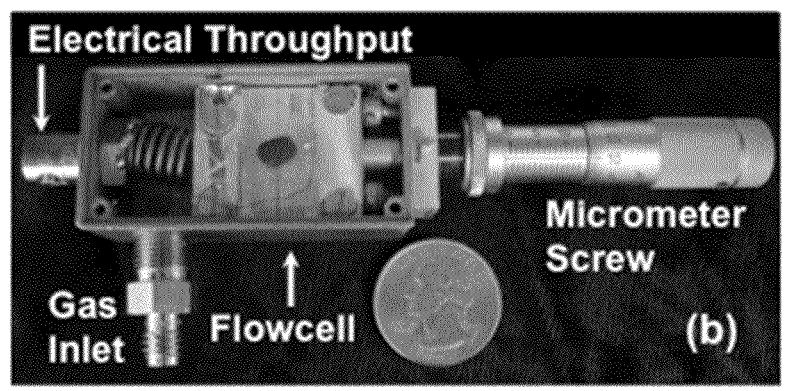
FIG. 4 is a photograph of a mechanical strain apparatus and chemiresistor sensor enclosed within a flowcell.

As shown in FIG. 4, the strain apparatus and sensor can be enclosed within a flowcell where the sensor can be exposed to analyte. In some embodiments, the flowcell can comprise an electric shielding box with gas inlet and outlet ports and electrical connections to supply the chemiresistor with a fixed voltage and to monitor the its change in conductance in situ.

Figure 5:
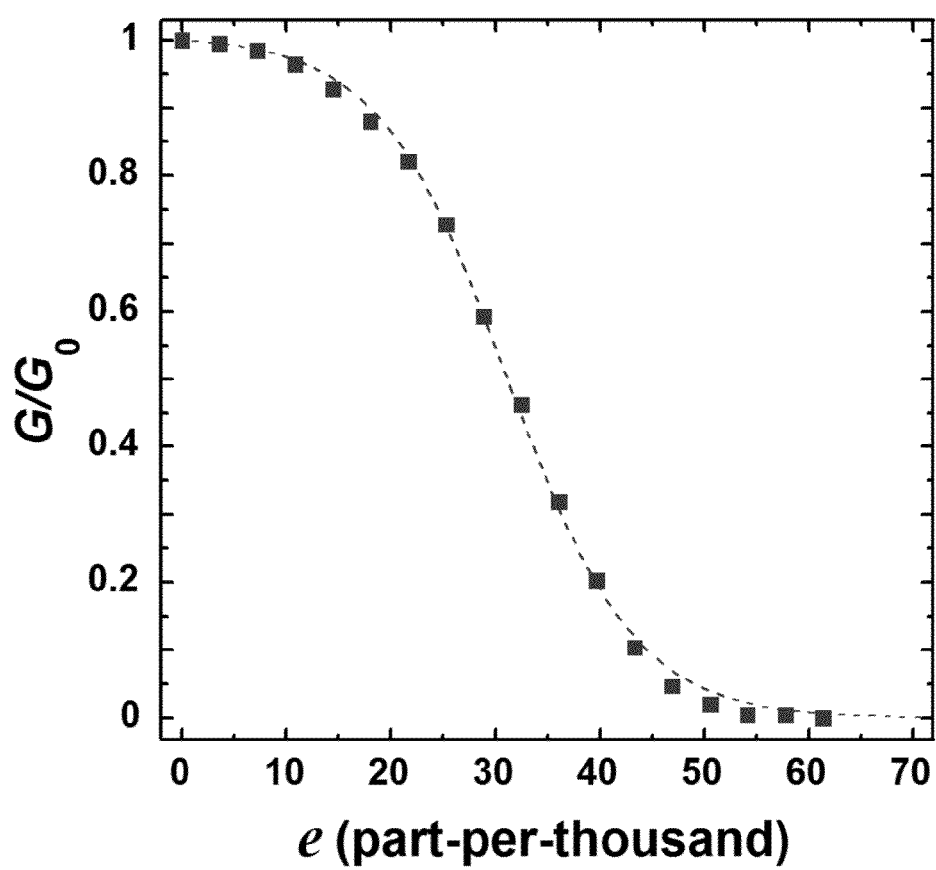
FIG. 5 is a graph of relative conductance ratio versus uniaxial strain (resulting from mechanical strain) for a field-structured chemiresistor.

The response of one embodiment using an FSCR to a uniaxial strain in part-per-thousand (ppt) is shown in FIG. 5.

Figure 6:
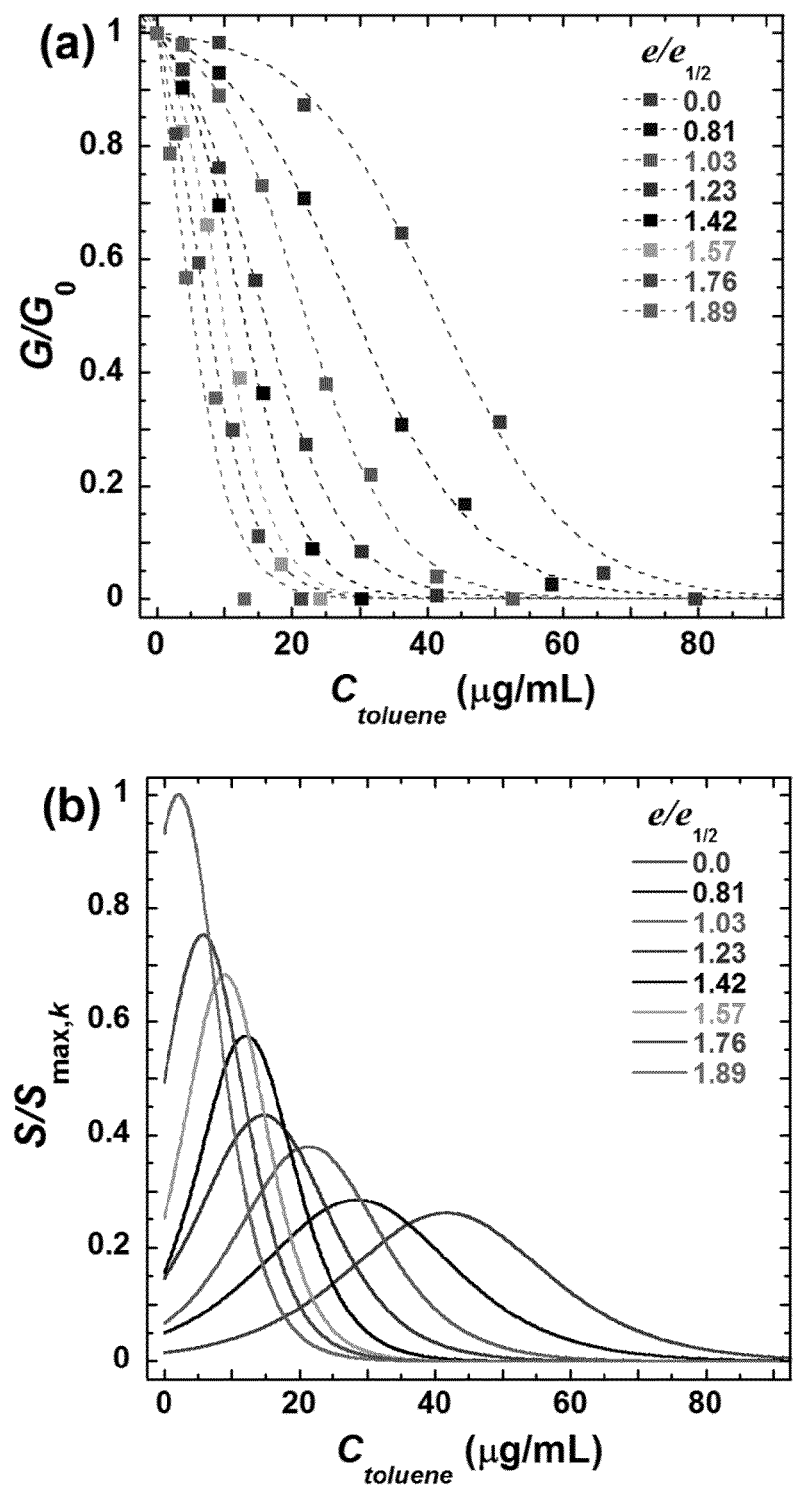
FIG. 6(a) is a graph of relative conductance ratio versus toluene concentration for the field-structured chemiresistor for various values of uniaxial tensile strain.
FIG. 6(b) is a graph of sensitivity versus toluene concentration for the field-structured chemiresistor for various values of uniaxial tensile strain.

The response of the FSCR to uniaxial tensile strain produces a sigmoidal transduction curve. Prior to analyte exposure, the sensor is mechanically strained until the desired baseline conductance is reached. The response of the sensor as a function of analyte concentration is then determined at the tuned baseline conductance. FIGS. 6(a) and (b) show the response of the mechanically strained sensor to toluene vapors for various prestrain values. The sigmoidal shape of the original (unstrained; $e/e_{1/2}=0$) response curve in FIG. 6(a) shows the relatively insensitive response of the sensor to low analyte concentrations. However, for the prestrained sensors, the sigmoidal shape changes and the initial slope increases dramatically, producing large changes in $G/G_0$ at the lower concentrations where the unstrained sensor displays low sensitivity. In the illustrated embodiment, the unstrained sensor reaches a 5% response ($G/G_0=0.95$) at 14.7 micrograms/mL, whereas for a pre-load strain of 58 ppt ($e/e_{1/2}=1.89$), the sensor reaches this same magnitude of response at only 0.525 micrograms/mL, corresponding to a 28-fold increase in sensitivity in this operating region.

Figure 7:
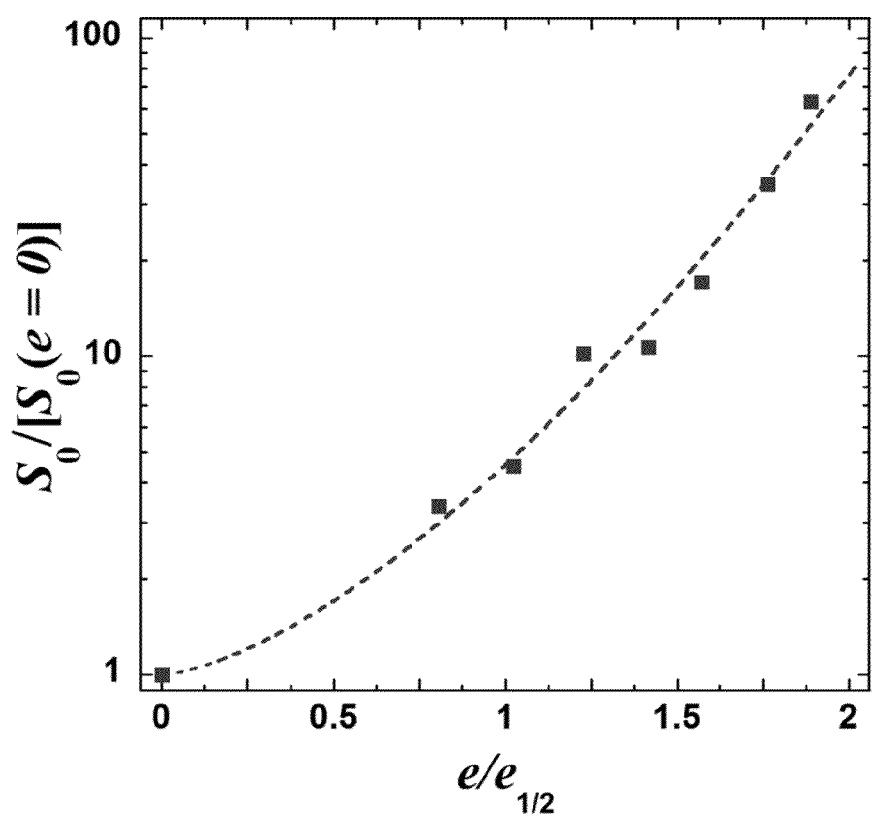
FIG. 7 is a plot of initial sensitivity relative to initial sensitivity at zero strain as a function of relative prestrain.

FIG. 7 is a plot of initial sensitivity ($S_0$) relative to initial sensitivity at zero strain ($S_0[e=0]$) as a function of relative prestrain. The increase in initial sensitivity is exponential in prestrain before reaching the sensor's maximum attainable sensitivity. The relative initial sensitivity, $S_0/S_0[e=0]$, is presented. The initial sensitivity is the slope of the sensor transduction curve in the limit of low analyte concentration. The initial sensitivity of the sensor at a particular preload strain (e) is $S_0$, and $S_0[e=0]$ is the initial sensitivity of the unstrained sensor. The increase in initial sensitivity is exponential in preload strain as seen as a straight line on semi-logarithmic axes. For the illustrated embodiment, the maximum sensitivity is approximately 62 times that of the unstrained sensor. FIG. 7 shows that a very small magnitude of preload strain produces a large increase in the initial sensitivity. This behavior is helpful because it allows the chemiresistor to have high sensitivity at very low analyte concentrations, thereby significantly lowering the lower detection limit of the sensor. Such ability to dynamically and reversibly tune the sensitivity of a single chemiresistor has not been available before this invention.

A more detailed description of the chemiresistor operation follows. When a chemiresistor is exposed to chemical vapors the polymer swells in proportion to the analyte concentration. This volumetric strain reduces the contact pressure between particles, increasing the sensor resistance. The response of an FSCR can be defined as its relative conductance ratio, $G/G_0$, where $G_0$ is its baseline conductance and G is the steady-state conductance in the presence of an analyte. Plotting $G/G_0$ as a function of analyte concentration results in the sigmoidal response curve shown in FIG. 1(a). Because the relative resistance change is exponential with analyte concentration, these conductance data can be fit by $$\frac{G}{G_0} = \left[1 + \frac{e^{\Gamma C/C_{1/2}} - 1}{e^{\Gamma} - 1}\right]^{-1}. \qquad (1)$$

where C is the analyte concentration, $\Gamma$ is a fit parameter related to the abruptness of the conductor/insulator transition, and $C_{1/2}$ is the response mid-point, defined as the analyte concentration that reduces $G_0$ by half.

The FSCR sensitivity is defined as the slope of the response curve at a specific analyte concentration:

$$S(C) \equiv -\frac{d(G/G_0)}{dC} = -\frac{\Gamma e^{\Gamma C/C_{1/2}}}{C_{1/2}(1-e^\Gamma)}\left[1+\frac{e^{\Gamma C/C_{1/2}}-1}{e^\Gamma-1}\right]^{-2}. \quad (2)$$

FIG. 1(b) illustrates how FSCR sensitivity varies over the sensing range. The maximum sensitivity occurs at the sensor's response mid-point, whereas at the upper and lower limits of the sensing range the sensitivity is quite low. The initial sensitivity of an FSCR is the slope in the limit of zero analyte concentration, $$S_0 \equiv \lim_{C \to 0} S = \frac{\Gamma}{C_{1/2}(e^\Gamma-1)}. \quad (3)$$

This initial sensitivity determines the sensor's lower detection limit (LDL). It is conventional to define the LDL as the concentration that gives a change in FSCR conductance three-times greater than the standard deviation of the baseline conductance, $\sigma_{G_0}$, $$\frac{G(LDL)}{G_0} \equiv 1 - \frac{3\sigma_{G_0}}{G_0}. \quad (4)$$

The LDL is then:

$$LDL = \frac{3\sigma_{G_0}}{S_0 G_0}. \quad (5)$$

In the following example, a 55-fold decrease in the sensor's LDL by increasing the initial sensitivity, $S_0$, through the application of a tensile strain is demonstrated. To apply a tensile strain, the sensor was formed on a flexible elastomeric substrate. A two-part, addition-cure (Pt-catalyzed) polydimethylsiloxane (PDMS) was used for both the substrate and the polymer phase of the FSCR composite. Other elastomeric materials can also be employed. The chemiresistor was made by mixing 15 vol. % gold-plated nickel particles into the viscous PDMS precursor and curing at 50° C. for four hours in a uniform 650 G magnetic field. Other conductive magnetic particles can also be used. The magnetic field vector was oriented such that particle chains form parallel to the substrate to span the electrode gap, as illustrated in FIG. 2. The particles were 3-7 μm spherical-agglomerate carbonyl nickel particles and were immersion gold plated. Conditions for gold plating will depend on the specific plating solution employed. The electrodes were made of gold mesh, and are partially encapsulated between the composite and the flexible substrate. A schematic drawing showing the mechanical strain apparatus and the modified chemiresistor is shown in FIG. 3.

The chemiresistor composite and gold-mesh electrodes were bonded to the substrate by placing them on the elastomeric substrate just before the substrate was fully cured (i.e., just after it reached its gel point). At this point, the substrate was still tacky to the touch, but was sufficiently solidified to be able to support the electrodes and the viscous chemiresistor composite precursor. Because the substrate was not yet fully cured, a fraction of unreacted functional groups can chemically bond with the curing chemiresistor composite. Chemical bonding of the chemiresistor to the substrate allows any strain within the substrate to be transferred directly to the chemiresistor with no slippage or delamination. This method has the added benefit of encapsulating the gold-mesh electrodes between the substrate and chemiresistor composite for robustness. Using an elastomer as the substrate and as the continuous phase of the chemiresistor composite also enables the induced strain to be reversible. Alternative methods for joining the chemiresistor sensing film, electrodes, and flexible substrate can also be employed in various embodiments.

The preceding description of the embodiment is presented in terms of a sensing film that is a field structured composite, but it is to be understood that other types of chemiresistor sensing films can be employed in other embodiments of the present invention.

The strain apparatus and sensor for this embodiment are enclosed in a shielded flowcell with gas inlet and outlet ports and electrical throughputs, as illustrated in FIG. 4. The tensile strain apparatus illustrated in FIG. 3 consists of two abutting, but separable, surfaces to which the elastomeric chemiresistor substrate is clamped at opposing ends. These separable surfaces are held together by a compressed spring until a micrometer-calibrated screw pushes the surfaces apart, stretching the elastomeric substrate and bonded chemiresistor composite. The uniaxial Cauchy strain of the FSCR, e, is the ratio of the change in length of the FSCR/substrate, ΔL, to the unstrained length, $L_0$: $e = \Delta L/L_0$. Although this illustrated embodiment employs a screw mechanism to strain the chemiresistor, one can envision using a wide variety of means of actuation, including but not restricted to piezoelectric materials, magnetostrictive materials, pistons, solenoids, and other mechanical devices suitable for changing the separation between the two halves of the tensioner substrate.

Known concentrations of analyte vapors were produced by mixing a controlled flowrate of analyte-saturated nitrogen from a temperature-controlled bubbler system with a controlled flow of pure nitrogen. Conductance measurements were made by applying a 10 mV DC voltage across the electrodes with a power supply and measuring the current with a picoammeter.

FIG. 5 shows the FSCR response to mechanically induced tensile strain, e. A fit of these data to Equation 1 yields the constants: Γ=5.09 and response mid-point, $e_{1/2}$=31.16 part-per-thousand ($R^2$=0.999). In this experiment each increasing step in strain caused an immediate drop in the FSCR conductance, which was followed by a relatively small conductance increase as the non-equilibrium component of the polymer stress relaxed. The conductance values in FIG. 5 are for this relaxed state. In the following, the tensile strain values are normalized by the response mid-point value ($e_{1/2}$) of 31.2 part-per-thousand strain.

To determine the effect of tensile strain on FSCR chemical response, the sensor was first strained in the absence of analyte to achieve the desired baseline conductance, and then the chemical response curve was obtained. FIG. 6(a) shows the response of the mechanically strained sensor to toluene for various prestrains, and FIG. 6(b) shows the corresponding sensitivity curves. The response curve for the unstrained sensor has the typical sigmoidal shape that gives low sensitivity at low analyte concentration. However, as the tensile strain increases there is a progressive change of this sigmoidal shape, and the curvature of the response curve becomes purely negative. The maximum sensitivity increases significantly with tensile strain, and the position of this maximum shifts towards zero analyte concentration. The change in the abruptness of the conductor/insulator transition is quantitatively evident from the decreasing Γ values in Table I. This single sensor can detect toluene concentrations between 0.051 and ~75 µg/mL—a range spanning nearly three decades.

The semi-log plot in FIG. 7 shows that the initial sensitivity increases super-exponentially with tensile strain. Even very small tensile strains result in substantial increases in FSCR initial sensitivity—as much as 62-times that of the unstrained sensor. An evaluation of the noise in the FSCR baseline conductance for both the unstrained and maximally strained ($e/e_{1/2}=1.89$) states yields standard deviations of $\sigma_{G_0}(e/e_{1/2}=0)=2.465\times10^{-3}$ mA and $\sigma_{G_0}(e/e_{1/2}=1.89)=2.976\times10^{-5}$ mA. Using initial sensitivity values from Table I and Equation 5, one calculates the LDLs as 2.80 and 0.051 µg/mL toluene respectively. This is a ~55-fold decrease in the FSCR's LDL between these strained and unstrained states. The difference between the values for the change in sensitivity versus the change in LDL is a result of the variation in the noise in the conductance baseline signals between the two states, which the initial sensitivity calculation does not take into account. Of course, standard noise reduction techniques could be used to increase the sensor sensitivity (modulation of the applied dc voltage, signal averaging, etc.).

TABLE I

Processed Experimental Data Corresponding to the Response Curves in FIG. 6(a)

| e(ppt) | $e/e_{1/2}$ | $G_0$ (mA) | $\Gamma$ | $C_{1/2}$ (µg/mL) | $R^2$ | $S_0$ (µg/mL)$^{-1}$ |
|---|---|---|---|---|---|---|
| 0.0 | 0.00 | 1.81 | 4.256 | 41.971 | 0.998 | 0.0015 |
| 25.2 | 0.81 | 1.32 | 3.137 | 29.349 | 0.999 | 0.0049 |
| 32.0 | 1.03 | 0.846 | 3.133 | 21.969 | 0.999 | 0.0065 |
| 38.3 | 1.23 | 0.43 | 2.470 | 15.895 | 1.000 | 0.0144 |
| 44.2 | 1.42 | 0.193 | 2.688 | 12.799 | 0.999 | 0.0153 |
| 48.9 | 1.57 | 0.094 | 2.375 | 9.837 | 0.993 | 0.0248 |
| 55.0 | 1.76 | 0.036 | 1.768 | 7.503 | 0.997 | 0.0485 |
| 58.8 | 1.89 | 0.019 | 1.310 | 5.275 | 0.967 | 0.0918 |

The preceding illustrative embodiment employs a split substrate tensioner, wherein changing the gap between two solid substrates is the primary mechanism for changing the tensile strain in the sensing film. An alternative means of providing variable and controlled tensile strain is by using a flexible substrate that is bent to provide tensile strain to an attached chemiresistor structure, wherein the chemiresistor structure comprises the sensing film, electrodes, and an elastic substrate. Other means of changing the strain can also be employed in various embodiments. Some other straining devices can employ shear strain or torsional strain.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for determining a concentration of an analyte with a chemiresistor sensor, comprising:
    providing a chemiresistor sensor;
    applying a mechanical strain to the chemiresistor sensor;
    exposing the strained chemiresistor sensor to the analyte; and
    measuring a conductance of the exposed chemiresistor sensor to determine the concentration of the analyte.

2. The method of claim 1, further comprising measuring a baseline conductance of the strained chemiresistor sensor prior to the exposing step and comparing the measured conductance of the analyte-exposed chemiresistor sensor to the baseline conductance.

3. The method of claim 1, wherein the chemiresistor sensor is strained prior to the exposing step to optimize a sensitivity of the sensor to the analyte.

4. The method of claim 1, wherein the mechanical strain comprises a uniaxial strain, shear strain, torsional strain, or a combination thereof.

5. The method of claim 1, wherein measuring the conductance comprises measuring the conductance across a gap between a pair of electrodes attached to the chemiresistor sensor.

6. The method of claim 1, wherein the chemiresistor sensor comprises a plurality of conducting particles in a strainable electrically insulating matrix.

7. The method of claim 6, wherein the conducting particles comprise gold, silver, platinum, copper, carbon, ferrite, cobalt, nickel, iron, gadolinium, chromium, or manganese.

8. The method of claim 6, wherein the strainable electrically insulating matrix comprises a polymer.

9. The method of claim 1, wherein the chemiresistor sensor comprises a field-structured composite.

10. The method of claim 9, wherein the field-structured composite comprises conducting magnetic particles in a polymeric matrix.

11. The method of claim 10, wherein the conducting magnetic particles comprise a conductive outer shell surrounding a magnetic core.

12. The method of claim 11, wherein the magnetic core comprises ferrite, cobalt, nickel, iron, gadolinium, chromium, or manganese.

* * * * *